United States Patent [19]

Cahoon et al.

[11] Patent Number: 5,654,402
[45] Date of Patent: Aug. 5, 1997

[54] METHODS AND COMPOSITIONS RELATING TO PLANT $\Delta^6$ PALMITOYL-ACYL CARRIER PROTEIN DESATURASE

[75] Inventors: Edgar B. Cahoon, Suffolk County, N.Y.; John B. Ohlrogee, Ingham County, Mich.

[73] Assignee: Michigan State University, East Lansing, Mich.

[21] Appl. No.: 329,560

[22] Filed: Oct. 26, 1994

[51] Int. Cl.[6] .......................... C07K 14/415; C12N 9/04; C12N 15/29
[52] U.S. Cl. ............... 530/377; 536/23.6; 800/DIG. 69; 530/370; 530/378
[58] Field of Search ................... 530/377, 370, 530/378; 800/DIG. 69; 536/23.6

[56] References Cited

U.S. PATENT DOCUMENTS 5,057,419  10/1991  Martin et al. ...................... 435/134

OTHER PUBLICATIONS

Cahoon et al 1994 (4 Nov.) J of Biol Sci 269(44): 27519–27526.
Topfer et al 1994 J. Plant Physiol 143: 416–425.
CA Abstract 112: 135397.
CA Abstract 108: 184585.
CA Abstract 106: 64688.
Cahoon et al 1994 (Mar.) Plant Physiol 104: 827–837.

*Primary Examiner*—Patricia R. Moody
*Attorney, Agent, or Firm*—Pioneer Hi-Bred International, Inc.

[57] ABSTRACT

A plant $\Delta^6$ palmitoyl-acyl carrier protein desaturase, the gene encoding the desaturase, and transgenic plants and plant cells containing the heterologous DNA encoding the desaturase are described. The desaturase introduces a double bond at the sixth carbon atom from the carboxyl end of a 16 carbon saturated fatty acid, and is therefore useful in production of plant seeds having a modified fatty acid profile.

3 Claims, 8 Drawing Sheets

```
Δ6  ATTTTGTAAAGTGAAAATGCCATTGGTATTCAAGACTATAGGAGCCCATAAGACTCCTCCTTGTACTTTAAATTTAGCTTCACCACCTTTGTACCAC   97
Δ6                M A L V F K S I G A H K T P P C T L N L A S P A L Y H    27
Δ9                M A L K L N P F L S Q T Q K L P S F A L P P M A S T R S  28
Δ4            M A M K L N A L M T L Q C P K R N M F T R I A P P Q A G R V R 31

Δ6  ACCACAGTCACAATGGCTTCCACTATTACTCACCCTCCCCCACTCAAAGAT...ACAAAAATATCGTCTACTCGACGA..GTAAGG.....   178
Δ6   T R V T M A S T I T H P P P L K D - - R K I S S T R R - V R - - -   54
Δ9   P K F Y : : : L K S G S K E V E N L K : P F M P P : E : H V Q V     61
Δ4   S K V S : : : L H A S : L V F : K L K A G R P - - - E : - - - -    57

Δ6  ACATATCCGTTGGCTCCACAGAAGGCTGAAATCTTCAATTCTATGCACGGGTGGGTTGAAGACACCATTCTCCCTTTCCTGAAGCCGGTGGAGCAGTCG 277
Δ6   T Y P L A P E K A E I F N S M H G W V E D T I L P F L K P V E E S   87
Δ9   : H S M P : Q : I : : : K : L D N : A : E N : : V H : : : : K C    94
Δ4   - - - - - - - D : L : : : L E : : A R : N : : V H : : S : : N :    82

Δ6  TGGCAGCCCGACGGACTTCCTCCCGGACTCCACTTCTGATGGGTTCCACGAGCAAGTGGAAGAGCTTCGTAAACGAACGGCCCATCTCCCTGATGATTAC 376
Δ6   W Q P T D F L P D S T S D G F H E Q V E E L R K R T A D L P D D Y   120
Δ9   : : : Q : : : : : : P A : : : D : : R : : E : A K E I : : :       127
Δ4   : : : Q : Y : : : P : : : A : E D : : K : M : E : A K : E : :     115

Δ6  TTAGTTGCATTGGTGGCAGCAATGGTGACGGAGGAAGCCCTTCCGACGTATCAAACAATGCTTAACACGACAGATGTCGATATACCATGAGAGCGGCGCC 475
Δ6   L V A L V G A M V T E E A L P T Y Q T M L N T T D V I Y D E S G A   153
Δ9   F : V : : : D : I : : : : : : : : : : : : : L : G V R : : T : :    160
Δ4   F : V : : : D : I : : : : : : M S : : : R C : G : K : D T : :      148

Δ6  AGCCCTGTGCCTTGGGCCGTTTGGACCCGGGCTTGGACCCGCTGAACAGAACAGGCATGGTCGATATTGTCAACAAGTATCTCTATCTTTCCCGTCGTGTC 574
Δ6   S P V P W A V W T R A W T A E E N R H G D I V N K Y L Y L S G R V   186
Δ9   : : T S : : : I : : : : : : : : : : : : : : L L : : : : : : :     193
Δ4   Q : T S : : T : : : : : : : : : : : : : : : L L : : : : : : :     181

Δ6  GATATGAAGCAAATTGAGAAGACTATTCAATACTTGATTGGCTCGGGCATGGATCCTGGTGCGGACAACAACCCGTACCTAGCATATATCTACACGTCG 673
Δ6   D M K Q I E K T I Q Y L I G S G M D P G A D N N P Y L A Y I Y T S  219
Δ9   : : R : : : : : : : : : : : : : : R T E : S : : : G F : : : :    226
Δ4   : : R M : : : : : : : : : : : : : T K T E : C : : M G F : : :    214

Δ6  TATCAGGAGAGGGCTACAGCGATCTCCCATGGAAGTCTGGGCCGGCTAGCGAGGCAGAAGGGAGAGATGAAACTGGCTCAGATTTGTGGAACAATTTCT 772
Δ6   Y Q E R A T A I S H G S L G R L A R Q K G E M K L A Q I C G T I S   252
Δ9   F : : : : : F : : : : : N T A : Q : K E H : D I : : : : : : A     259
Δ4   F : : : : : F : : : A N T A K : : Q H Y : D K N : : : V : : N : A 247

Δ6  GCCCGATGAGAAGCGGCACGAGCCGCCCGTACTCCAAAATCCTGGACAAGCTATTCGAGTTGGATCCAGAAGGCACAATGTTGGCGTTGGCATACATGATG 871
Δ6   A D E K R H E A A Y S K I V E K L F E L D P E G T M L A L A Y M M   285
Δ9   : : : : : : : : T : : T : : : : : I : : D : : V : : F : D : :    292
Δ4   S : : : : : : : A T : : T : : : : : A : I : : D T : V I : F S D : : 280

Δ6  AAGATGAAGATTGTAATCCCAGCTCGTCTGATGCACGATGGGAAGGATCCCGGACATGTTTCAACATTTCTCTGCTGTGTCCCAGCCACTGGGGATTTAC 970
Δ6   K M K I V M P A R L M H D G K D P D M F Q H F S A V S Q R L G I Y   318
Δ9   R K : : S : : H : Y : : R : D N L : D : : : : A : : : : V :      325
Δ4   R K : : Q : : A H A : Y : : S : D M L : K : : T : : : : Q I : V   313

Δ6  ACTGCAAAGCAGTATACCGACATTCTGGAGCATATGATAGCCCCGGTGGGAGTGGATAAGCTGACGGGGCTGAGCGGGCAGGCCCCAGCCCCAGGAT 1069
Δ6   T A K E Y T D I L E H M I A R W G V D K L T G L S G E G R R A Q D   351
Δ9   : : : D : A : : : : F L V G : : K : : : : : : A : : : Q K : :   358
Δ4   S : W D : C : : : D F L V D K : N : A : M : : : : : : : : K : : E 346

Δ6  TACCGTGTGCCGGGTTGCCCATGAGGTTTAGGAAGGTGGAGGAGAGGGCCCAGCCGTGGCCCGACAATATATCGGCAT...GTTCCTTTTAGCCTGGATCTTT 1165
Δ6   Y V C G L P H R F R K V E E R A Q A W A E N I S H - V P F S W I F   383
Δ9   : : : R : : P : I : R L : : : : : G R : K E A P T - M : : : :   390
Δ4   : : : S : A A K I : R : : : K V : G K E K K A V L P V A : : : : :  379

Δ6  GGGACAAGACTG......TAGTCTCAGTCTCAGTCTCACTCGGTCACTGTGTTGTTTGTTCTATGATCAACAAATAAGTGCAATGCCACCCTTATTCTC 1258
Δ6   G R R V - - *                                                    387
Δ9   : : : : : :                                                      396
Δ4   : : : : : :                                                      385
```

FIG.5

METHODS AND COMPOSITIONS RELATING TO PLANT $\Delta^6$ PALMITOYL-ACYL CARRIER PROTEIN DESATURASE

FIELD OF THE INVENTION

The present invention relates to plant fatty acid desaturases. More particularly, the present invention relates to plant $\Delta^6$ palmitoyl-acyl carrier protein desaturases, the genes encoding such desaturases, transgenic plants and plant cells containing DNA encoding such desaturases, and methods for altering the fatty acid profile of plant seeds through the use of such desaturases.

BACKGROUND

Fatty acid desaturases of plants have received considerable attention because of their contributions to the physiology and economic value of plants. The activity of fatty acid desaturases, for example, may be a component of the ability of certain species to adjust levels of membrane unsaturation in response to stresses such as chilling (1–3). In addition, the degree of fatty acid unsaturation resulting from desaturase activity is often a major determinant of the nutritional and industrial quality of plant seed oils (4).

Plants typically contain a variety of fatty acid desaturases. The most numerous of these are membrane-associated desaturases that use fatty acids bound to glycerolipids as substrates (5). In addition, the synthesis of oleic acid ($18:1\Delta^9$) in plants and certain other organisms such as Euglena (photoauxotrophic) is catalyzed by a desaturase that functions on fatty acids esterified to acyl carrier protein (ACP) (6–8). This enzyme, the $\Delta^9$ stearoyl (18:0)-ACP desaturase (EC 1.14.99.6), displays soluble activity in contrast to all previously characterized desaturases (6). In the presence of radiolabeled 18:0-ACP and cofactors including NADPH, ferredoxin (Fd), and ferredoxin-NADPH reductase, the activity of the $\Delta^9$18:0-ACP desaturase is readily detectable in extracts of most plant tissues (9). Due in part to its soluble nature and relative ease of assay, the $\Delta^9$18:0-ACP desaturase has been purified from several plant sources (10–14), and a number of cDNAs encoding this enzyme have been isolated (12–20). In addition to the $\Delta^9$18:0-ACP desaturase, a $\Delta^4$16:0-ACP desaturase has recently been identified in plants (21, 22). This enzyme is a component of the petroselinic acid ($18:1\Delta^6$) biosynthetic pathway in endosperm of coriander (*Coriandrum sativum* L.) and other Umbelliferae species. Translation of a cDNA for the $\Delta^4$16:0-ACP desaturase has revealed that this enzyme shares extensive amino acid identity with the $\Delta^9$18:0-ACP desaturase (21).

The existence of structurally related acyl-ACP desaturases with different substrate recognition and double bond-positioning properties offers the opportunity to compare the active site structures of members of this family of enzymes using techniques such as site-directed mutagenesis and x-ray crystallography. Information gained from this research could potentially lead to the design of desaturases capable of producing new industrially useful isomers of monounsaturated fatty acids. These studies would be aided by the isolation of cDNAs for other variant acyl-ACP desaturases in addition to those for the $\Delta^9$18:0- and $\Delta^4$16:0-ACP desaturases. A potential source of such a desaturase is seed of *Thunbergia alata* (Acanthaceae family). The oil of this tissue consists of more than 80% weight of the unusual fatty acid $\Delta^6$ hexadecenoic acid ($16:1\Delta^6$) (23). We have used biochemical and molecular biological approaches to examine whether $16:1\Delta^6$ is synthesized by the activity of a unique acyl-ACP desaturase that is related to the $\Delta^9$18:0- and $\Delta^4$16:0-ACP desaturases.

SUMMARY

The present invention therefore relates to an isolated $\Delta^6$ palmitoyl acyl carrier protein desaturase and DNA encoding same, transgenic plants and plant cells containing heterologous DNA encoding said desaturase, mRNA derived from DNA encoding such a desaturase, and vectors containing DNA encoding the desaturase. The present invention also relates to a method for modifying the fatty acid content of a plant seed involving the introduction of a double bond at the sixth carbon atom from the carboxyl end of the saturated 16 carbon fatty acid, for example palmitic acid. Additionally, the present invention relates to plant seeds having a modified fatty acid content derived through the method of the invention.

An objective of the invention is to provide a mechanism for the modification of fatty acids in order to enhance the industrial and nutritional quality of plant seed oils. As part of this invention, we have developed a method for introducing a double bond at a novel position in a saturated fatty acid. The invention entails the identification of the enzyme (a $\Delta^6$-palmitoyl-acyl carrier protein desaturase) involved in the biosynthesis of the unusual fatty acid $\Delta^6$-hexadecenoic acid. In addition, a complementary DNA (cDNA) was isolated for this desaturase. Expression of the cDNA in *Escherichia coli* resulted in the production of a catalytically active $\Delta^6$-palmitoyl-acyl carrier protein desaturase.

This invention offers the opportunity to synthesize a monounsaturated fatty acid with a double bond positioned at the sixth carbon atom from the carboxyl end of the fatty acid molecule. The invention also allows for unsaturation to be introduced into a saturated 16 carbon fatty acid (palmitic acid). These two features of the invention allow for the production of a monounsaturated fatty acid that is not normally found in conventional plant seed oils. The major monounsaturated fatty acid present in seed oils is oleic acid, an 18 carbon fatty acid with a double bond positioned at the ninth carbon atom from the carboxyl end of the molecule.

The ability of the invention to introduce a double bond into palmitic acid offers the potential for reducing the saturated fatty acid content of vegetable oils. Typically, the presence of the 16 carbon saturated fatty acid palmitic acid limits the nutritional quality of seed oils. Therefore, the invention may allow for the production of a seed oil with reduced palmitic acid content. As a result, such an oil would presumably be less harmful to human health.

In addition, the product of the invention, $\Delta^6$-hexadecenoic acid, may be useful as a chemical precursor of certain industrial feedstocks. Because the double bond of $\Delta^6$-hexadecenoic acid is located at the sixth carbon atom, this fatty acid can be oxidatively cleaved to form adipic acid (a six carbon dicarboxylic acid) and decanoic acid (a ten carbon fatty acid). Adipic acid is a precursor of nylon 66 and is currently derived from petroleum by-products.

Furthermore, the use of $\Delta^6$-hexadecenoic acid has been proposed as an emollient in cosmetics (U.S. Pat. No. 4,036, 991).

ACP(16:0). The Std. lane contains methyl [1-$^{14}$C]16:0 (16:0), [1-$^{14}$C]18:1Δ$^9$(Δ$^9$), and [1-$^{14}$C]18:1Δ$^6$(Δ$^6$).

Figure 2:
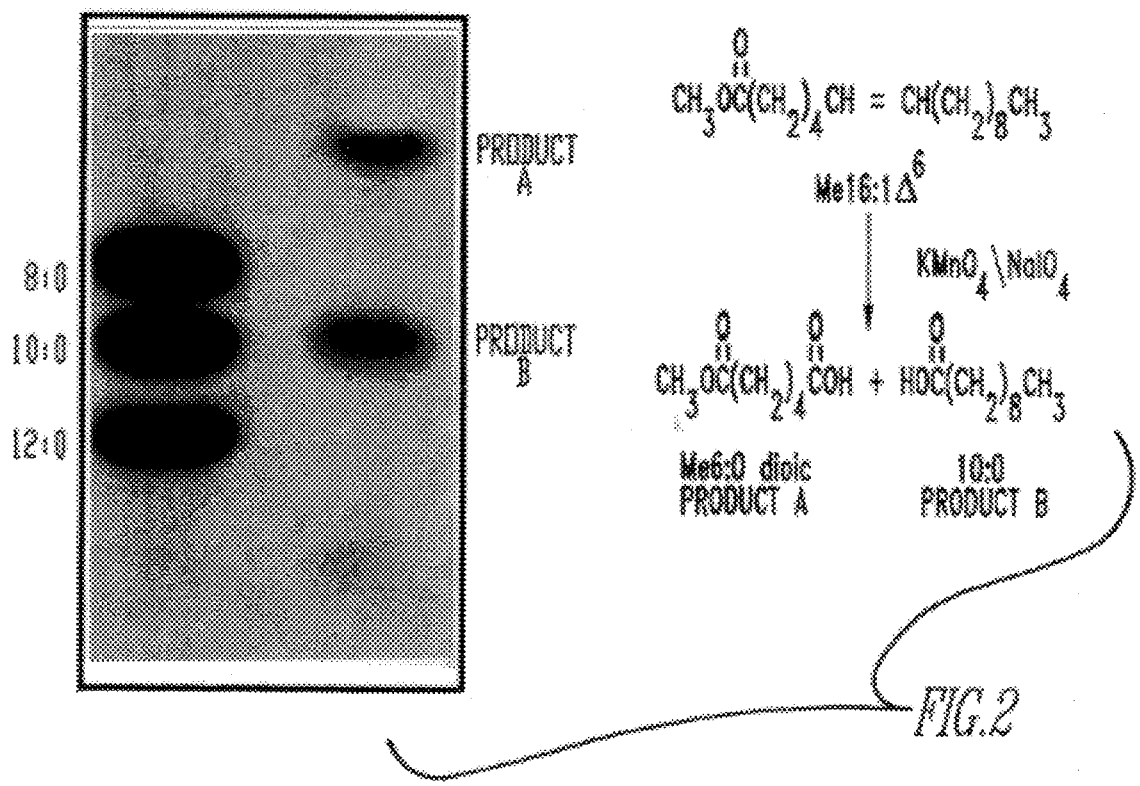

FIG. 2 is an autoradiogram of oxidized products of [$^{14}$C]16:0-ACP desaturase assays. Shown are the permanganate-periodate oxidation products of the methyl ester derivatives of 16:1 formed by acyl-ACP desaturation activity in *T. alata* endosperm homogenates. [U-$^{14}$C]16:0-ACP was used as the substrate for this assay.

Figure 3:
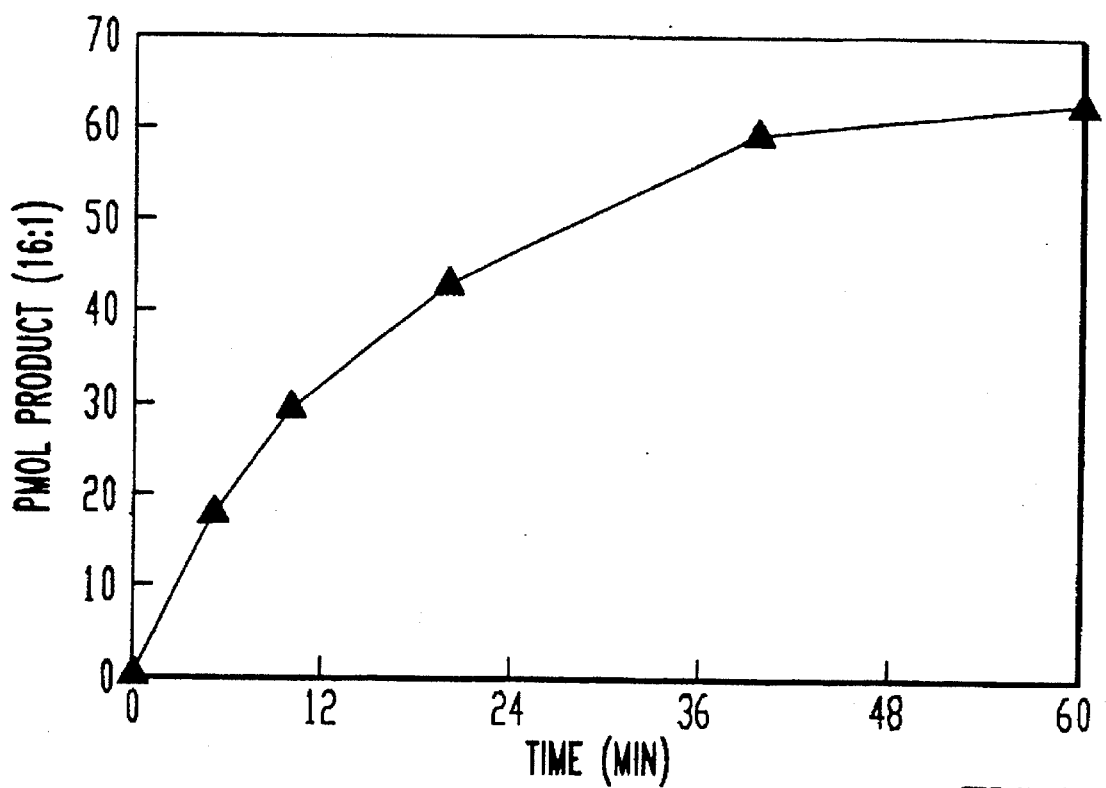

FIG. 3 shows the time course of [1-$^{14}$C]16:0-ACP desaturase activity in a 100,000×g supernatant of a *T. alata* endosperm homogenate. Assays were conducted with 118 pmol of [1-$^{14}$C]16:0-ACP and 23 μg of protein.

Figure 4:
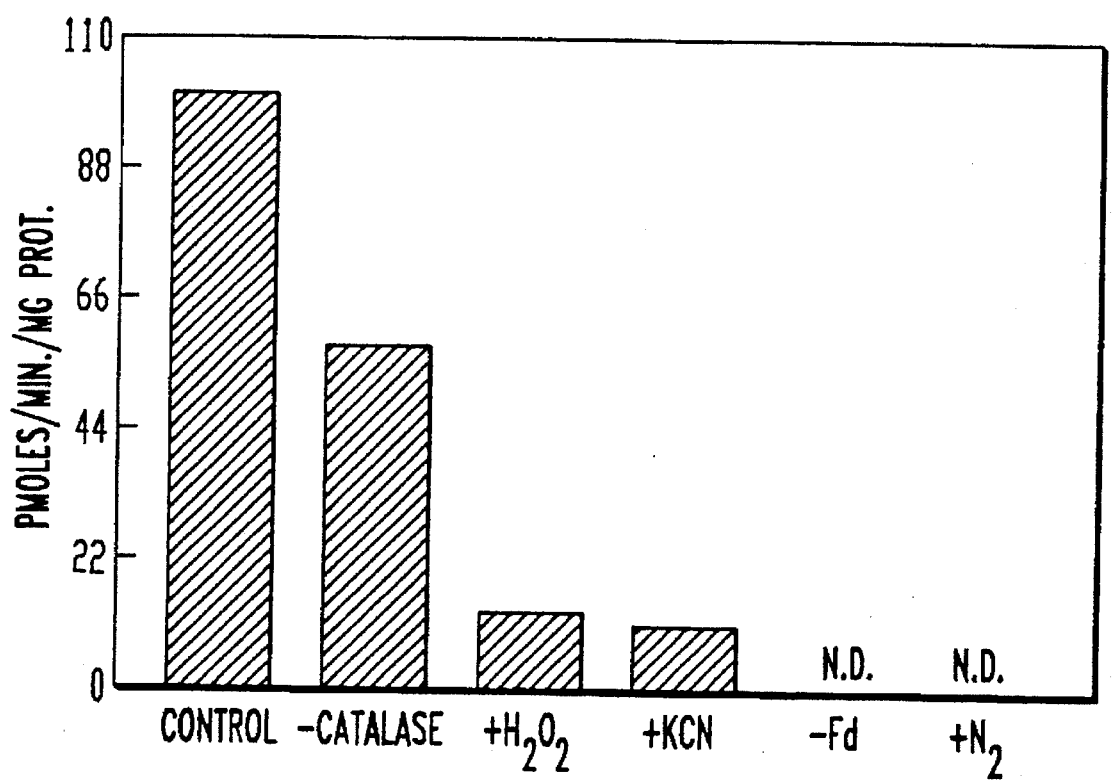

FIG. 4 shows the effect of catalase, ferredoxin (Fd), nitrogen (N$_2$), potassium cyanide (KCN), or hydrogen peroxide (H$_2$O$_2$) on Δ$^6$16:0-ACP desaturase activity in *T. alata* endosperm extracts. Assays were conducted for 10 min using 118 pmol of [1-$^{14}$C]16:0-ACP and 23 μg of protein from a 100,000×g supernatant of endosperm homogenate. Assays with potassium cyanide and hydrogen peroxide contained 1 mM of each compound, and catalase was omitted from assays containing hydrogen peroxide. (n.d.-not detected).

FIG. 5 is the nucleotide sequence (SEQ ID NO: 1) of the cDNA insert of pTAD4 (Δ$^6$) and a comparison of the deduced amino acid sequences (SEQ NOS 2-4) of pTAD4 (Δ$^6$) and cDNAs for the coriander Δ$^4$16:0-ACP desaturase (Δ$^4$) (see Ref. 21) and the castor Δ$^9$18:0-ACP desaturase (Δ$^9$) (see Ref. 13). Identical amino acids are indicated by colons. Amino acids that are absent relative to the castor Δ$^9$18:0-ACP desaturase are indicated by dashed lines. Alignment of the nucleotide sequence of the cDNA insert of pTAD4 is maintained with a dotted line. The underlined alanine at amino acid 33 is the likely start of the native peptide encoded by pTAD4.

Figure 6:
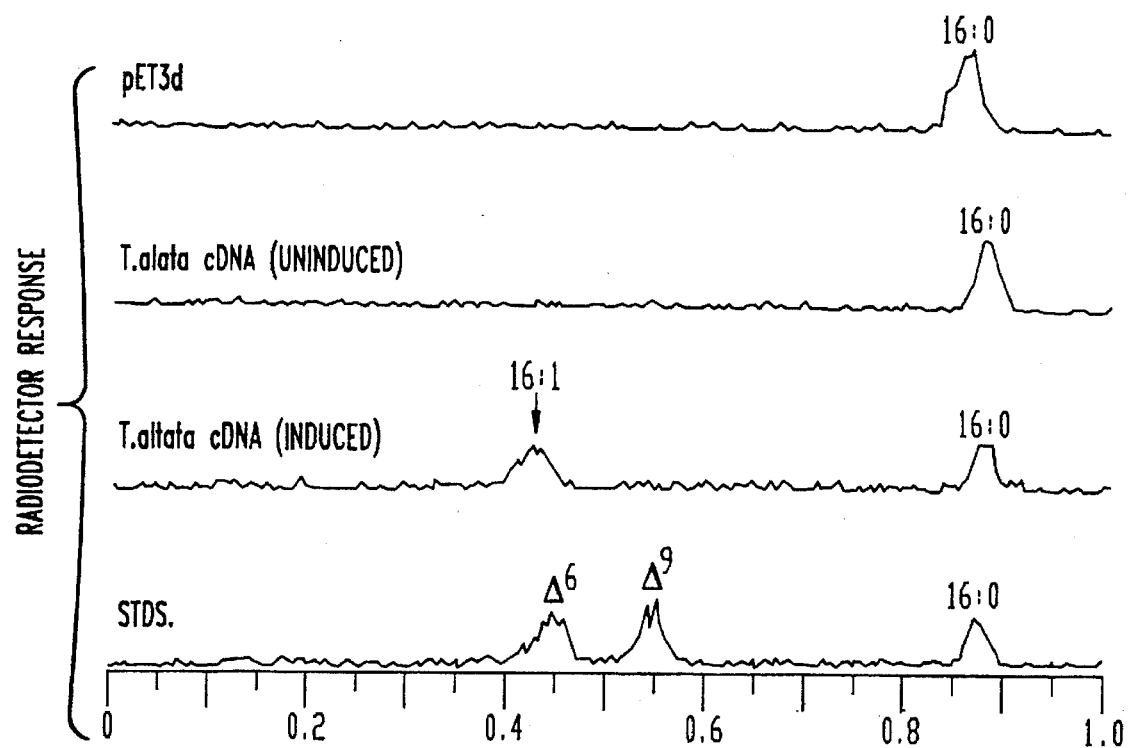

FIG. 6 compares the Δ$^6$16:0-ACP desaturase activity of extracts of *E. coli* BL21 pLysS containing only the vector pET3d or pET3d with insert derived from the *T. alata* cDNA of pTAD4 (with or without isopropyl-1-thio-β-D-galactopyranoside induction). The methyl ester of 16:1 formed by the *E. coli*-expressed desaturase was separated from methyl 16:0 of the unreacted substrate by argentation TLC as shown. Assays were conducted for 60 min using 230 μg of *E. coli* protein and 118 pmol of [1-$^{14}$C]16:0-ACP. Shown in the standard chromatogram are (std.) are methyl [$^{14}$C]16:0, -18:1Δ$^9$, and -18:1Δ$^6$.

Figure 7:
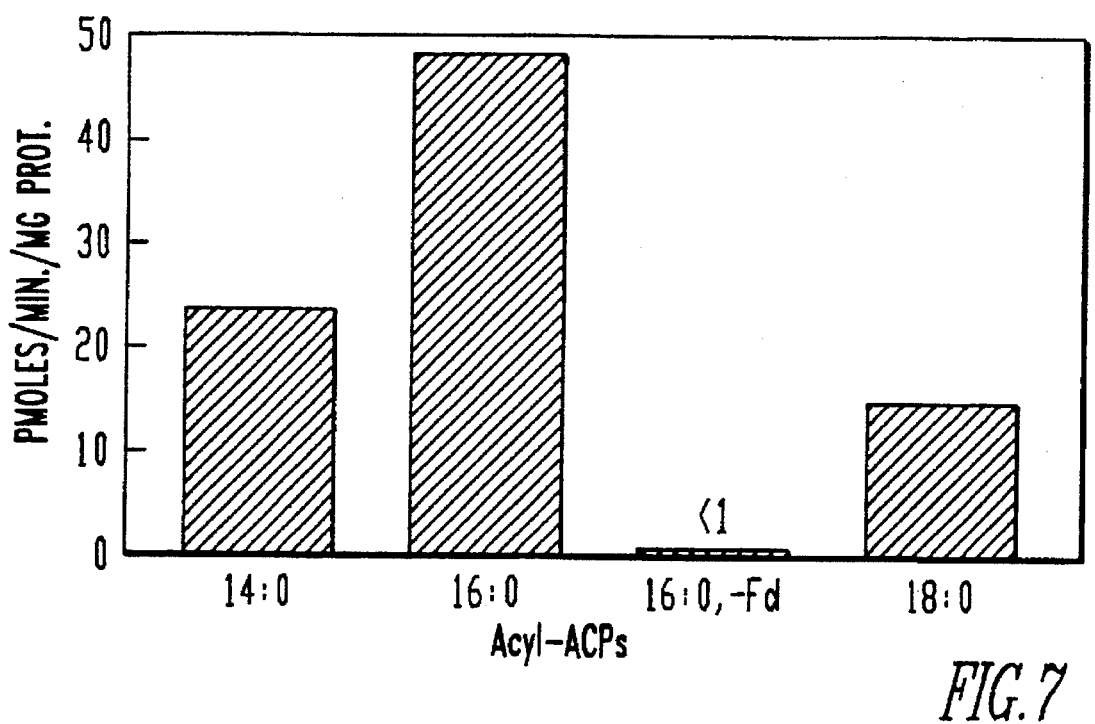

FIG. 7 shows substrate specificity and ferredoxin dependence of the *E. coli*-expressed *T. alata* Δ$^6$16:0-ACP desaturase encoded by the cDNA insert of pTAD4. Assays were performed for 10 minutes using 118 pmol of either [1-$^{14}$C] 14:0-, 16:0-(±ferredoxin, Fd), or 18:0-ACP and 65 μg of total *E. coli* protein.

Figure 8:
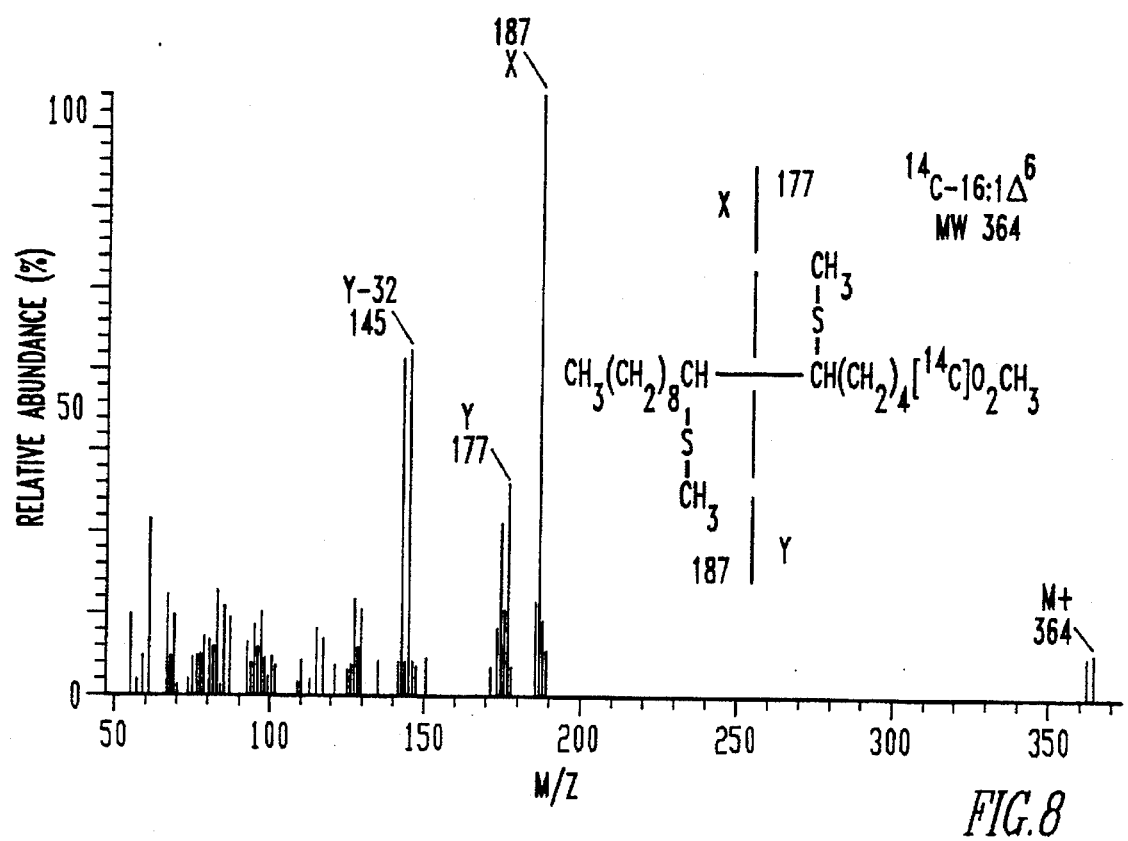

FIG. 8 shows a mass spectrum of derivatives of [1-$^{14}$C] 16:1 formed by 16:0-ACP desaturase activity in extracts of *E. coli* expressing the mature peptide-coding region of pTAD4. The [1-$^{14}$C]16:1 desaturation product was converted to a methyl ester derivative and reacted with dimethyl sulfoxide prior to mass spectral analysis.

DETAILED DESCRIPTION

Experimental Procedures

Plant Material—Studies were conducted using developing endosperm dissected from fruits of *T. alata* Bojer ex Sims (black-eyed susan vine) (Northrup King, Minneapolis, Minn.). Fruits were collected from plants grown either outdoors in pots during summers in East Lansing, Mich. or under greenhouse conditions with natural illumination. In the latter case, flowers required hand pollination for adequate fruit set. Endosperm was frozen in liquid nitrogen following dissection and stored at −70° C. until use in enzyme assays of RNA extraction.

Acyl-ACP Desaturation Assays—Approximately 200–300 mg of developing *T. alata* endosperm was homogenized in 3 ml of buffer consisting of 100 mM Tris-HCl, pH 7.5, 2.5 mM dithiothreitol, 1 mM isoascorbate, 10% (v/v) glycerol, and 1.5% (w/v) polyvinylpolypyrrolidone using an Elvehjem tissue grinder. Debris and polyvinylpolypyrrolidone were subsequently removed by centrifugation at 14,000×g for 5 min. The supernatant was then passed through two layers of miracloth (Calbiochem) and spun for an additional 10 min at 30,000×g. The soluble phase was removed while attempting to avoid recovery of the floating fat layer. A portion of contaminating fat was extracted by passing the supernatant through glass wool loosely packed in a Pasteur pipette. The supernatant from the 30,000×g spin was further clarified by centrifugation at 100,000×g for 60 min. All centrifugation steps were performed at 5° C. The resulting supernatant was used immediately for desaturation assays described below or frozen in aliquots in liquid N$_2$ and stored at −70° C. until further use. Of note, extracts developed a brown color, presumably due to extensive phenolic oxidation, when maintained at −20° C. for longer than 1–2 weeks.

Acyl-ACP desaturation assays were based on those previously described (8, 9). Assays were performed in a total volume of 150 μl in loosely capped 13×100-mm glass tubes and consisted of 1.25 mM NADPH (from a freshly prepared stock in 100 mM Tricine, pH 8.2), 3.3 mM ascorbate, 0.7 mM dithiothreitol, 8000 units of bovine liver catalase (Sigma), 5 μg of bovine serum albumin (Fraction V) (Sigma), 20 μg of spinach ferredoxin (Sigma), 80 milliunits of spinach ferredoxin:NADPH reductase (Sigma), 33 mM PIPES, pH 6.0, and 118 pmol of [1-$^{14}$C] acyl-ACP or -CoA. Reactions were started with the addition of the 100,000×g supernatant of homogenized *T. alata* endosperm (typically 20–25 μg of total protein) and were conducted at room temperature (−22° C.) with shaking (100 revolutions/min). Assays were terminated with the addition of 850 μl of 2.35M NaOH and carrier fatty acids (30 μg of palmitic and petroselinic acid). The stopped reactions were then heated at 85° C. for 1 hour. Following acidification with 350 μl of 4M H$_2$SO$_4$, the resulting free fatty acids were recovered by three extractions with 2.5 ml of hexane. Fatty acids were converted to methyl ester derivatives with 10% (w/v) boron trichloride in methanol (Alltech) using the method described by Morrison and Smith (24). Reaction products were then analyzed on 15% AgNO$_3$ TLC plates developed sequentially to heights of 10 and 20 cm in toluene at −20° C. TLC plates were prepared as described previously (25). Radioactivity was detected by autoradiography and quantified by liquid scintillation counting of TLC scrapings in a non-aqueous complete mixture.

To confirm the identity of 16:1Δ$^6$ produced from palmitoyl-ACP, assays were conducted as described above using [U-$^{14}$C] palmitoyl-ACP as the substrate. The methyl ester derivative of the monounsaturated product was purified by argentation TLC as described above and eluted from TLC scrapings with hexane/ethyl ether (2:1, v/v). The monounsaturated methyl ester was then cleaved at its double bond using permanganate-periodate oxidation (26). Chain lengths of oxidation products were determined relative to [$^{14}$C] fatty acid standards by reverse-phase TLC using a mobile phase of acetonitrile/methanol/water (75:25:0.5).

Inhibition of desaturase activity was examined by supplementing assays with 1 mM KCN (neutralized) or 1 mM $H_2O_2$. In the latter case. catalase was omitted from reactions. Oxygen dependence of desaturase activity was characterized by purging assay tubes completely with nitrogen prior to and after addition of plant extract, and the reaction tube was tightly capped for the duration of the assay.

Radiolabeled acyl-ACPs were synthesized enzymatically using *Escherichia coli* ACP according to the method of Rock and Garwin (27). The following fatty acids were used in the synthesis of acyl-ACPs: [1-$^{14}$C] myristic acid (American Radiolabeled Chemicals, St. Louis, Mo.) (specific activity 55 mCi/mmol), [1-$^{14}$C] palmitic acid (NEN Dupont) (specific activity 58 mCi/mmol), [U-$^{14}$C] palmitic acid (NEN Dupont) (specific activity 800 mCi/mmol), and [1-$^{14}$C] stearic acid (American Radiolabeled Chemicals) (specific activity 55 mCi/mmol). [1-$^{14}$C] Palmitoyl-CoA (specific activity 52 mCi/mmol) was purchased from Amersham Corp. A [$^{14}$C] petroselinic acid standard was prepared by incubation of coriander endosperm slices in [1-$^{14}$C] acetate as described previously (25).

*T. alate* Endosperm cDNA Library Construction—Total RNA was isolated from *T. alate* endosperm using the method of Hall et al. (28). RNA was then passed through a cellulose (Sigma Cell 50, Sigma) column in order to reduce amounts of polysaccharides potentially recovered along with the RNA.

Poly(A)$^+$ RNA was enriched by passing total RNA once through a column of oligo (dT) cellulose (Pharmacia LKB Biotechnology Inc.) and subsequently used in the construction of a Uni-ZAP XR (Stratagene) cDNA expression library according to the instructions of the manufacturer. A portion of the total amplified library packaged in phage was mass excised (29) yielding pBluescript II SK(−) harboring cDNA inserts. The recovered plasmid DNA was used for cDNA isolation by colony hybridization and polymerase chain reaction (PCR) amplification as described below.

PCR Amplification of Nucleotide Sequences Encoding Acyl-ACP Desaturases—Fully degenerate sense and antisense oligonucleotides were prepared that corresponded respectively to the conserved amino acid sequences (SEQ ID NOS 10 and 12) Gly-Asp-Met-Ile-Thr-Glu-Glu and Glu-Lys-Thr-Ile-Gln-Tyr-Leu present in $\Delta^9$18:0 - (13, 15–20) and $\Delta^4$16:0-ACP desaturases (21). The sequence of the resulting sense and antisense oligonucleotides (SEQ NOS 5 and 6) were 5'-GG(A/C/G/T)GA(C/T)ATGAT(A/C/T)AC(A/C/G/T)GA(A/G)GA-3' and 5'-A(A/G)(A/G)TATTG(A/G/T)AT(A/C/G/T)GT(C/T)TT(C/T)TC-3', respectively. Included on the 5' terminus of each oligonucleotide was sequence (5'-CAUCAUCAUCAU-3' or 5'-CUACUACUACUA-3', SEQ ID NOS 7 and 8) that allowed for insertion of PCR products into the pAMP1 vector (Life Technologies, Inc.). Template for PCR amplification was generated by transformation of the SOLR strain (Stratagene) of *E. coli* with an aliquot of the mass-excised *T. alata* endosperm cDNA library. Following growth of transformed *E. coli* to stationary phase in 3 ml of liquid culture, plasmid DNA was purified for use as template in PCR amplification. Reactions were performed in a 50-μl volume and consisted of 10 μM sense and antisense oligonucleotides, 150–300 ng of plasmid DNA derived from the *T. alata* cDNA library, 2 mM $MgCl_2$, 0.2 mM dNTPs, 1×Taq reaction buffer (Life Technologies, Inc.), and 5 units of Taq polymerase (Life Technologies, Inc.). Temperature conditions for PCR amplification were 5 min at 95° C. and 25 cycles of 1 min at 95° C., 1.5 min at 55° C., and 1.5 min at 72° C. This was followed by an additional 10 min extension at 72° C. PCR fragments of approximately 215 base pairs were gel-purified, ligated into the pAMP1 vector using the CloneAmp system (Life Technologies, Inc.) according to the manufacturer's protocol, and introduced into *E. coli* DH5a (Life Technologies, Inc.). The resulting colonies were screened using colony hybridization as described by Sambrook et al. (30). A "negative" screening protocol was Used to reduce the chances of reisolating cDNAs (pTAD1, 2, and 3) encoding $\Delta^9$18:0-ACP desaturases that were previously obtained by antibody screening of the *T. alata* endosperm cDNA library (19). DNA probes for library screening were formed by PCR amplification of portions of pTAD 1, 2, and 3. Primers and PCR reaction conditions were the same as those described above. An equimolar mixture of the PCR products derived from pTAD1, 2, and 3 was used as template for the synthesis of [$\propto$-$^{32}$P]dCTP random-primed labeled probes. Hybridization of plasmids of lysed colonies with radiolabeled probes was carried out in 6×SSC and 0.25% (w/v) non-fat dry milk with shaking for 4 hours at 53° C. as described by Sambrook et al. (30). Filters were washed three times in 1×SSC and 0.1% SDS at 60° C. (45 min/wash) and exposed to autoradiography. Plasmid DNA was subsequently isolated from 10 colonies which displayed little or no hybridization to the probes. Nucleotide sequence of the inserts of these plasmids was obtained by dideoxy chain termination using Sequenase 2.0 (United States Biochemical Inc.) according to the manufacturer's instructions. Two classes of plasmids were identified (designated pEC6 and 7), both of which contained inserts encoding portions of apparent acyl-ACP desaturases (based on amino acid identity with known $\Delta^9$18:0- and $\Delta^4$16:0-ACP desaturases).

Screening of a *T. alata* Endosperm cDNA Library for a Full-length Divergent Acyl-ACP Desaturase—Aliquots of the mass excised *T. alata* endosperm cDNA library were used to transform *E. coli* SOLR cells. Approximately 50,000 colonies were screened using colony hybridization as described previously (30). Nucleotide probes for screening were generated by [$\propto$-$^{32}$P]dCTP random-primed hexamer labeling of inserts of pEC6 and 7. Hybridization and washing conditions were the same as those described above. Colonies containing plasmid DNA that strongly hybridized to the probe derived from pEC6 were isolated, and nucleotide sequence was obtained from both strands of the longest cDNA insert (the corresponding plasmid was designated pTAD4) using Sequenase 2.0. Because of a relative lack of abundance, colonies containing plasmid hybridizing to the pEC7-derived probe were not further characterized.

*E. coli* Expression of a Putative cDNA for $\Delta^6$ Palmitoyl-ACP Desaturase—To determine the activity of the desaturase encoded by pTAD4, the portion of the clone corresponding to the mature peptide (total protein minus plastid transit peptide) was expressed in *E. coli*. This region of the cDNA insert of pTAD4 was first amplified by PCR using Vent DNA polymerase (New England Biolabs). The nucleotide sequence of the sense primer was 5'-GCTTCGACTATTACTCAC3-(SEQ ID NO:9). M-13(-20) forward primer was used as the antisense oligonucleotide. The PCR product was blunt-end ligated into the NcoI site of the *E. coli* expression vector pET3d (Novagen) as described (30). The NcoI-digested vector had been previously treated with the Klenow fragment of DNA polymerase I to fill-in 5' protruding ends. The junction between the vector and the 5' terminus of the insert was sequenced to confirm that the PCR product was ligated into pET3d in the proper reading frame. This construct was subsequently introduced into the *E. coli* strain BL21 pLysS and grown in LB media with carbenicillin (125 μg/ml) and chloroamphenicol (30 μg/ml) selection. At a cell density of $OD_{600}$~0.8, cultures were induced with the addition of isopropyl-1-thio-β-D-galactopyranoside to a final concentration of 0.5 mM and grown for an additional 4 hours. Cells were then washed in 50 mM Tris-HCl, pH 7.5, lysed by two freeze-thaw cycles (using a liquid nitrogen bath for freezing and a 22° C. water bath for thawing). Lysates were then incubated with bovine pancreas DNase I (Boehringer Mannheim) (20 μg/ml) for 15 min at 22° C. The extract was subsequently centrifuged at 14,000×g for 5 min. The resulting supernatant was used for acyl-ACP desaturation assays as described above. Radiolabel in the TLC-analyzed reaction products was detected using a Bioscan System 200 image scanner. The double bond position of the monounsaturated product was determined by gas chromatography-mass spectrometry analysis of its dimethyl disulfide derivative (31). In these studies, the desaturation assays described above were scaled up 6-fold, and reactions were conducted with 2.6 nmol of [1-$^{14}$C]16:0-ACP and 1.1 mg of soluble protein of lysed *E. coli* expressing the *T. alata* cDNA. Assays were conducted for 4 hours. High protein concentrations and long incubation periods were used to ensure the synthesis of sufficient amounts of monounsaturated fatty acid for mass spectral analyses. Reaction products were converted to fatty acid methyl esters as described above and subsequently reacted with 100 μl of an iodine solution (60 mg/ml ethyl ether) and 350 μl of dimethyl disulfide (Aldrich). After 3 hours of incubation with shaking (250 revolutions/min) at 37° C., dimethyl disulfide derivatives of unsaturated fatty acid methyl esters were extracted as described previously (32). These derivatives (dissolved in hexane) were then analyzed by gas chromatography-mass spectrometry using a Hewlett Packard PH589011 gas chromatograph interfaced with a HP5971 mass selective detector. Separation of analytes was achieved using a DB23 (30 m×0.25 mm inner diameter) column (J&W Scientific) with the oven temperature programmed from 185° C. (3 min hold) to 230° C. at rate of 2.5° C./min.

Results

Figure 1:
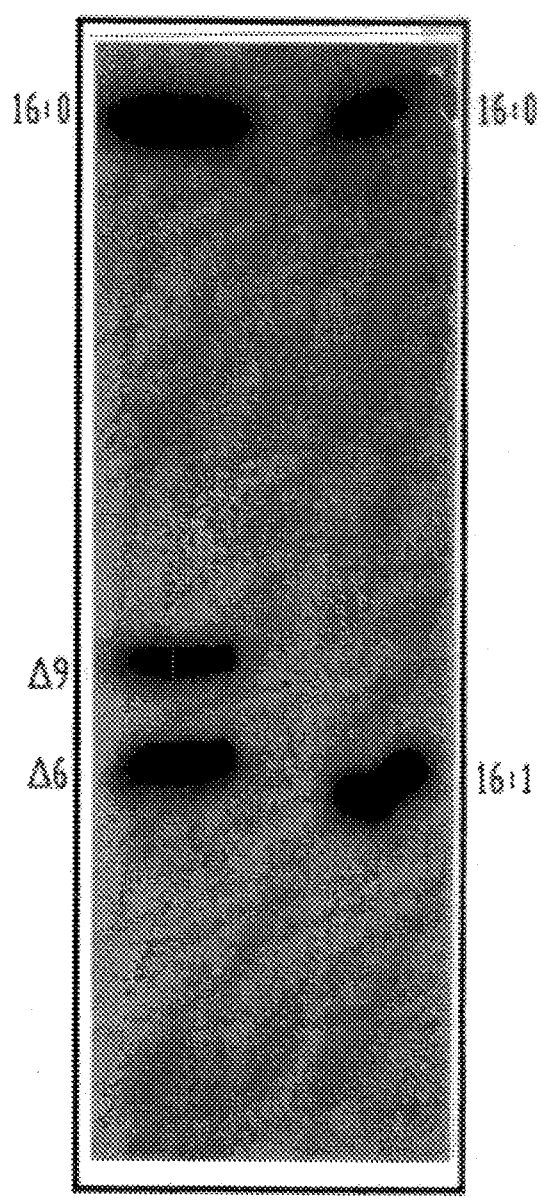
FIG. 1 is an autoradiogram of intact products of [$^{14}$C] 16:0-ACP desaturase assays conducted with a 100,000×g supernatant of *T. alata* endosperm extracts (16:1), and the methyl ester of 16:0 derived from unreacted [1-$^{14}$C]16:0-

Detection of a Soluble $\Delta^6$ Palmitoyl-ACP Desaturase in *T. alata* Endosperm Extracts—The seed oil of *T. alata* is composed of nearly 85% weight of the unusual monounsaturated fatty acid $\Delta^6$ hexadecenoic acid (16:1$\Delta^6$). To examine the metabolic origin of the double bond of this fatty acid, the 100,000×g supernatant of a homogenate of developing *T. alata* seed endosperm was incubated with [$^{14}$C]16:0-ACP and potential desaturase cofactors. Using this assay system, substantial amounts of 16:0-ACP desaturase activity were detected in the soluble endosperm extract (FIG. 1). In the absence of a radiolabeled standard for 16:1$\Delta^6$, two independent analytical methods indicated that the double bond of the resulting 16:1 moiety was positioned at the $\Delta^6$ carbon atom: 1) the 16:1 desaturation product displayed mobility on argentation TLC plates similar to that of the $\Delta^6$ monounsaturated fatty acid petroselinic acid (18:1$\Delta^6$) when these molecules were analyzed as methyl ester derivatives (FIG. 1) and 2) permanganate-periodate oxidation of the methyl ester of the 16:1 desaturation product gave rise to a molecule with mobility on reverse-phase TLC equivalent to that of decanoic acid (10:0) (FIG. 2, Product B) as well as to an acyl moiety containing a lesser number of carbon atoms (FIG. 2, Product A).

Substrate Properties of the $\Delta^6$ Acyl-ACP Desaturase—To confirm that the $\Delta^6$ desaturase identified above is most active with 16:0-ACP, assays were conducted using $^{14}$C-saturated acyl-ACP substrates containing 14, 16, and 18 carbons. As with 16:0-ACP (described above), $\Delta^6$ desaturase activity was also detected when [1-$^{14}$C]14:0- and 18:0-ACP were reacted with a 100,000×g supernatant of a *T. alata* endosperm homogenate. Following derivitization, a portion of the desaturation products resulting from 18:0-ACP comigrated on argentation TLC with the methyl ester of petroselinic acid, which was resolvable in this system from methyl oleic acid (data now shown). Similarly, the desaturation product arising from 14:0-ACP migrated in the expected position for a fatty acid containing a $\Delta^6$ double bond (data not shown). Therefore, it appears that the $\Delta^6$ desaturase of *T. alata* endosperm positions the placement of unsaturation with regard to the carboxyl end of fatty acid substrates. This double bond positioning property has been previously observed with the $\Delta^9$18:0- and $\Delta^4$16:0-ACP desaturases (22, 33).

Under the assay conditions used, $\Delta^6$16:0-ACP desaturase activity in the 100,000×g supernatant of a *T. alata* endosperm homogenate was essentially linear over 10 min (FIG. 3). When assays were conducted over this time period, the specific activity of the $\Delta^6$ desaturase was approximately 7-fold higher using [1-$^{14}$C]16:0-ACP as a substrate rather than either [1-$^{14}$C]14:0- or 18:0-ACP (Table 1). Values obtained with the latter substrate, however, were obscured because of the presence of completing $\Delta^9$18:0-ACP desaturase activity in the endosperm extract. Finally, no desaturase activity was detected when [1-$^{14}$C]16:0-CoA was presented as a potential substrate. Overall, these results indicate that the $\Delta^6$ desaturase is most active in vitro with 16:0 esterified to ACP.

TABLE I

In vitro substrate specificities of acyl-ACP or -CoA desaturases of *T. alata* endosperm
Desaturase assays were conducted for 10 min using 118 pmol of [1-$^{14}$C]acyl-ACP or -CoA substrate and 23 μg of total protein from 100,000 × g supernatant of a *T. alata* endosperm homogenate.

| Substrate | Monounsaturated products[a] | |
|---|---|---|
| | $\Delta^6$ | $\Delta^9$ |
| | pmol/min/mg protein | |
| 14:0-ACP | 13 | ND[b] |
| 16:0-ACP | 99 | ND |
| 16:0-CoA | ND | ND |
| 18:0-ACP | 12 | 173[c] |

[a]14:1$\Delta^6$18:1$\Delta^6$, and 18:1$\Delta^9$ were identified by the mobilities of these fatty acids on argentation TLC plates.
[b]Not detected.
[c]Assay conditions were adjusted only for the linear measurement of $\Delta^6$ desaturase activity. Therefore this value may underestimate the specific activity of $\Delta^9$18:0-ACP desaturase.

Cofactors and Inhibitors of $\Delta^6$ Palmitoyl-ACP Desaturase Activity—Additional in vitro assays were conducted to compare the functional properties of the $\Delta^6$16:0-ACP desaturase with those previously determined for the $\Delta^9$18:0-ACP desaturase (7, 8, 10). In this regard, virtually no $\Delta^6$16:0-ACP desaturase activity was detected in the 100,000×g supernatant of *T. alata* endosperm homogenates when assays were conducted in the absence of ferredoxin or molecular oxygen (FIG. 4). $\Delta^6$16:0-ACP desaturase activity was also reduced when catalase was omitted from assays. Furthermore, the inclusion of 1 mM KCN or $H_2O_2$ in reactions resulted in the loss of most of the desaturase activity. Such catalytic properties of the *T. alata* $\Delta^6$16:0-ACP desaturase were similar to those previously described for the $\Delta^9$18:0-ACP desaturase (7, 8, 10).

Isolation of a cDNA Encoding a Diverged Acyl-ACP Desaturase from *T. alata* Endosperm—Based on functional similarities of the $\Delta^6$16:0 - and $\Delta^9$18:0-ACP desaturases described above, we examined whether these enzymes are also structurally related. To address this question, attempts were made to isolate a cDNA for the $\Delta^6$16:0-ACP desaturase using $\Delta^9$18:0-ACP desaturase-derived probes. As a first approach, a cDNA expression library prepared from poly (A)* RNA of T. alata endosperm was screened with antibodies against the $\Delta^9$18:0-ACP desaturase of avocado (13). This method was previously used to obtain a cDNA for the $\Delta^4$16:0-ACP desaturase of coriander endosperm (21). In the present study, however, antibody screening of the T. alata endosperm expression library yielded only cDNAs for three apparent isoforms of the $\Delta^9$18:0-ACP desaturase, which were designated pTAD1, 2, and 3 (19).

As an alternative approach, PCR amplification of a $\Delta^6$16:0-ACP desaturase-specific nucleotide probe was attempted using degenerate sense and antisense oligonucleotides prepared against two conserved amino acid sequences in $\Delta^9$18:0- and $\Delta^4$16:0-ACP desaturases. One of the sequences, SEQ ID NO: 10 (Gly-Asp-Met-Ile-Thr-Glu-Glu) is encoded by the cDNA for the $\Delta^4$16:0-ACP desaturase and all known cDNAs for the $\Delta^9$18:0-ACP desaturase. The second sequence (SEQ ID NO: 11) (Glu-Lys-Thr-Ile-Gln-Tyr-Leu) is also encoded by the $\Delta^4$16:0-ACP desaturase cDNA and all known $\Delta^9$18:0-ACP desaturase cDNAs except that of safflower (14). Products of approximately 215 base pairs obtained following one round of PCR amplification of the total T. alata cDNA library (in plasmid form) were screened after subcloning into the pAMP1 vector. To delineate products of the previously isolated cDNAs pTAD1, 2, and 3, colonies containing PCR-derived clones were screened in a negative manner with random-labeled probes for pTAD1, 2, and 3 and conditions of moderate to high stringency. One of the resulting clones (pEC6) that displayed weak or no hybridization to these probes encoded an amino acid sequence that was somewhat diverged from those of known $\Delta^9$18:0-ACP desaturases.

When the T. alata endosperm library was screened with a random-labeled probe prepared from the insert of pEC6, >0.1% of the total cDNAs examined strongly hybridized to this probe. The longest of a selected portion of these cDNAs (the corresponding plasmid was designated pTAD4) contained 1279 base pairs and had an open-reading frame corresponding to a 387-amino-acid polypeptide with considerable identity to known $\Delta^4$16:0- and $\Delta^9$18:0-ACP desaturases (FIG. 5). Based on similarity of flanking bases to the consensus sequence proposed by Lütcke et al. (34), the translational start site of the cDNA insert of pTAD4 likely occurs at nucleotide 17. In addition, from homology with $\Delta^4$16:0- and $\Delta^9$18:0-ACP desaturases, the mature peptide encoded by pTAD4 likely begins at amino acid 33. As such, the 32 amino acids preceding this residue correspond to a putative plastid transit peptide as is present in all acyl-ACP desaturases characterized to date.

Interestingly, the cDNA insert of pTAD4 lacks nucleotide sequence for 6–7 amino acids found near the amino terminus of all previously characterized $\Delta^9$18:0-ACP desaturases. This region is also altered in the cDNA for the coriander $\Delta^4$16:0-ACP desaturase (21) as compared to cDNAs for $\Delta^9$18:0-ACP desaturases. In this case, the coding sequence for 15 amino acids is absent in the $\Delta^4$16:0-ACP desaturase cDNA relative to the castor $\Delta^9$18:0-ACP desaturase cDNA (13) (FIG. 5). The pTAD4-encoded peptide also contains 2 less amino acids at its carboxyl terminus than both the $\Delta^4$16:0- and $\Delta^9$18:0-ACP desaturases. Despite these differences, the interior regions of the putative desaturase encoded by pTAD4 share significant identity with portions of the primary structures of $\Delta^4$16:0- and $\Delta^9$18:0-ACP desaturases, and the spacing between conserved regions of amino acids is the same in all three desaturase types. Overall, the mature peptide encoded by the cDNA insert of pTAD4 shares 66% identity with the castor $\Delta^9$18:0-ACP desaturase and 57% identity with the coriander $\Delta^4$16:0-ACP desaturase, disregarding any missing amino acids.

Activity of an E. coli-expressed cDNA for a Diverged Acyl-ACP Desaturase of T. alata Endosperm—To determine the activity of the desaturase corresponding to the cDNA insert of pTAD4, the mature peptide-encoding region of this clone was expressed in E. coli with expression driven by the T7 RNA polymerase promoter of the vector pET3d (Novagen). When assayed with [1-$^{14}$C]16:0-ACP, crude extracts of isopropyl-1-thio-$\beta$-D-galacto-pyranoside-induced recombinant E. coli catalyzed the synthesis of [$^{14}$C]16:1 (FIG. 6). In addition, the methyl ester of the 16:1 product displayed mobility on argentation TLC plates similar to that of a methyl petroselinic acid (18:1$\Delta^6$) standard, suggesting that this monounsaturated product is a $\Delta^6$ isomer. Detectable acyl-ACP desaturase activity was absent in extracts of E. coli harboring the pET3d vector without cDNA insert or in uninducted recombinant E. coli. Furthermore, like the activity found in T. alata endosperm extracts, the desaturase expressed in E. coli displayed an in vitro substrate preference for 16:0-ACP and exhibited no detectable activity in the absence of reduced ferredoxin (FIG. 7).

The [$^{14}$C]16:0 moiety produced in vitro from the E. coli-expressed desaturase was conclusively identified as a $\Delta^6$ isomer through gas chromatography-mass spectrometry analysis of its dimethyl disulfide derivative (FIG. 8). In the mass spectrum shown, the ions 145, 177, 187, and 364 m/z are diagnostic for a [1-$^{14}$C]16:1$\Delta^6$ moiety. Significant amounts of non-radiolabeled or [$^{12}$C]16:1$\Delta^6$ were also detected among the desaturase assay products. This was indicated by the presence of the additional ions 143, 175, and 362 m/z in the mass spectrum of [1-$^{14}$C]16:1$\Delta^6$ as well as by an enrichment in the abundance of ions 187 m/z (FIG. 8). It is unlikely that the non-radiolabeled 16:1$\Delta^6$ resulted from in vivo synthesis in E. coli. In this regard, E. coli does not normally produce 16:1$\Delta^6$ (35). Furthermore, gas chromatographic analysis of fatty acids of E. coli expressing the pTAD4-encoded desaturase failed to detect any 16:1$\Delta^6$ in the bacterial lipids (data now shown). Given the relatively high concentrations of E. coli protein used in these assays, unlabeled 16:1$\Delta^6$ likely arose from the in vitro desaturation of endogenous E. coli 16:0-ACP present in crude bacterial extracts.

Of note, expression levels of the T. alata cDNA in E. coli appeared to be low relative to that often obtained with DNA inserts placed behind the T7 RNA polymerase promoter (36). The expressed protein, for example, could not be distinguished on Coomassie-stained SDS-polyacrylamide gels of either the total soluble or insoluble protein fractions of lysed E. coli (data not shown). Also suggestive of low expression levels in E. coli, the specific activity of $\Delta^6$16:0-ACP desaturase in recombinant E. coli extracts (FIG. 7) was typically half of that detected in T. alata endosperm homogenates (Table I).

The results presented here demonstrate the involvement of a novel soluble $\Delta^6$16:0-ACP desaturase in the synthesis of $\Delta^6$ hexadecenoic acid in the endosperm of T. alata. The activity of this enzyme has several properties similar to those previously described for the $\Delta^9$18:0-ACP desaturase. These include the requirement of reduced ferredoxin for detectable in vitro activity, the stimulation of activity by catalase, and the inhibition of activity by potassium cyanide and hydrogen peroxide. The existence of a $\Delta^6 16:0$-ACP desaturase in *T. alata* endosperm was confirmed by the isolation of a cDNA for this enzyme. While the amino acid sequence deduced from this cDNA shares some identity with $\Delta^9 18:0$- and $\Delta^4 16:0$-ACP desaturases, these findings, together with those previously obtained for petroselinic acid biosynthesis (19, 21), indicate that natural variations in the primary structures of acyl-ACP desaturases can give rise to novel enzymes with altered substrate recognition and double bond positioning properties.

The major difference between the primary structures of the mature $\Delta^6 16:0$-, $\Delta^4 16:0$-, and $\Delta^9 18:0$-ACP desaturases occurs in a region near their amino termini. In this region, the *T. alata* $\Delta^6 16:0$-ACP desaturase contains 6 less amino acids than the castor $\Delta^9 18:0$-ACP desaturase. Similarly, this portion of the coriander $\Delta^4 16:0$-ACP desaturase lacks 15 amino acids relative to the castor $\Delta^9 18:0$-ACP desaturase. Without intending to be limited to any particular theory, one possibility is that differences in recognition of substrate chain length (16:0-ACP versus 18:0-ACP) and/or double bond positioning of these desaturases are associated with this divergence in the primary structures of these enzymes. Alternatively, this region of the amino terminus of $\Delta^9 18:0$-ACP desaturase may not contribute significantly to the catalytic properties of this enzyme. As such, while again not intending to be limited to any particular theory, if the $\Delta^4$ and $\Delta^6 16:0$-ACP desaturases evolved from the $\Delta^9 18:0$-ACP desaturase, then there may have been little selective pressure to maintain this region intact in the variant 16:0-ACP desaturases.

Ultimately, an understanding of how differences in the amino acid sequences of $\Delta^4 16:0$-, $\Delta^6 16:0$-, and $\Delta^9 18:0$-ACP desaturases contribute to variations in their functional properties will require comparisons of the three-dimensional structures of these enzymes. In this regard, elucidation of the crystal structure of the castor $\Delta^9 18:0$-ACP desaturase is currently in progress (37). With such information, it will be possible to overlap amino acid sequences of the $\Delta^4$ and $\Delta^6 16:0$-ACP desaturases onto the three-dimensional structure of $\Delta^9 18:0$-ACP desaturase to more precisely identify residues associated with the different substrate recognition and double bond positioning properties of these enzymes. This could eventually lead to the design of "tailor-made" desaturases that are capable of inserting double bonds into a variety of positions of acyl moieties of a range of carbon chain lengths.

An interesting observation from the studies described above was the lack of detectable amounts of $16:1\Delta^6$ in lipids of *E. coli* expressing the *T. alata* cDNA. Similarly, Thompson et al. (14) reported that expression of the safflower $\Delta^9 18:0$-ACP desaturase cDNA did not lead to the in vivo production of oleic acid in recombinant *E. coli*. The latter result can be explained by the fact that *E. coli* contains little 18:0-ACP (38). However, 16:0-ACP is a major component of the acyl-ACP pool of *E. coli*. Therefore it is unlikely that the lack of $16:1\Delta^6$ synthesis in *E. coli* expressing the *T. alata* cDNA is due to the presence of insufficient substrate for the desaturase. In addition, *E. coli* has been reported to contain ferredoxin (39), the apparent electron donor for the $\Delta^6 16:0$-ACP desaturase. However, as proposed by Thompson et al. (14), *E. coli* ferredoxin may not functionally interact with plant acyl-ACP desaturases. Alternatively, *E. coli* may not have adequate amounts of ferredoxin in a reduced form as required for $\Delta^6 16:0$-ACP desaturase activity.

In addition to $16:1\Delta^6$, *T. alata* seed contains the unusual fatty acid $18:1\Delta^8$, which composes about 2% weight of the oil of this tissue (23). We have previously shown that petroselinic acid ($18:1\Delta^6$) is formed by elongation of $16:1\Delta^4$-ACP in Umbelliferae endosperm (22). In an analogous manner, we predict that $18:1\Delta^8$ arises from the elongation of $16:1\Delta^6$-ACP rather than from the $\Delta^8$ desaturation of 18:0-ACP. Unlike the synthesis of petroselinic acid, though, elongation of 16:1-ACP in *T. alata* endosperm is likely not a major pathway as the ratio of amounts of $16:1\Delta^6:18:1\Delta^8$ in this tissue is approximately 40:1. In contrast, the ratio of amounts of $16:1\Delta^4:18:1\Delta^6$ in endosperm of the Umbellifarae coriander is more than 1:500 (22, 25).

Finally, significant efforts have been directed toward the development of transgenic crops that produce high value specialty oils (4, 40, 41). Using methodologies currently well known in the art, transgenic plants could be produced (42, 43) which would contain and express the $\Delta^6 16:0$-ACP desaturase gene and which would produce high levels of $16:1\Delta^6$. In this regard, oils rich in $16:1\Delta^6$ may have properties suitable for industrial use. Like petroselinic acid, $16:1\Delta^6$ can be oxidatively cleaved at its double bond to yield adipic acid, a precursor of nylon 6,6. In addition, high palmitic acid (16:0) mutants of crop plants including soybean (44) and *Brassica campesteris* (45) are available that could serve as appropriate backgrounds for transgenic expression of the cDNA for the *T. alata* $\Delta^6 16:0$-ACP desaturase. Still the success of such research would likely require additional studies to determine whether enzymes other than $\Delta^6 16:0$-ACP desaturase are specialized for the synthesis and metabolism of $16:1\Delta^6$ in *T. alata* endosperm. For example, a petroselinoyl-ACP-specific thioesterase has been identified in Umbelliferae endosperm extracts that efficiently releases petroselinic acid from ACP and, as a result, makes this fatty acid available for subsequent storage in triacylglycerol (46). A related enzyme may also be required for high levels of $16:1\Delta^6$ accumulation in transgenic plants.

References

1. Cheesbrough, T. M. (1990) *Plant Physiol.* 93, 555–559.
2. Wada, H., Gombos, Z., and Murata, N. (1990) *Nature* 347, 200–203
3. Miquel, M., James Jr., Dr. Dooner, H., and Browse, J. (1993) *Proc. Natl. Acad. Sci. U.S.A.* 90, 6208–6212.
4. Battey, J. F., Schmid, K. M., and Ohlrogge, J. B. (1989) *Trends Biotech.* 7, 122–125.
5. Heinz, E. (1993) in *Lipid Metabolism in Plants* (Moore, T. S., ed) pp. 33–89, CRC Press, Boca Raton, Fla.
6. Nagai, J., and Bloch, K. (1965) *J. Biol. Chem.* 240, 3702–3703.
7. Nagai, J., and Bloch, K. (1968) *J. Biol. Chem.* 243, 4626–4633.
8. Jaworski, J. G., and Stumpf, P. K. (1974) *Arch. Bochem. Biophys.* 162, 158–165.
9. McKeon, T. A., and Stumpf, P. K. (1981) *Methods Enzymol.* 71, 275–281.
10. McKeon, T. A., and Stumpf, P. K. (1982) *J. Biol. Chem.* 257, 12141–12147.
11. Cheesbrough, T. M., and Cho, S. H. (1990) in *Plant Lipid Biochemistry: Structure and Utiliziaton* (Quinn, P. J., and Harwood, J. L., eds) pp. 129–130, Portland Press, London.
12. Kinney, A. J., Hitz, W. D., and Yadav, N. S. (1990) in *Plant Lipid Biochemistry: Structure and Utilization* (Quinn, P. J., and Harwood, J. L., eds) pp. 126–128, Portland Press, London.

13. Shanklin, J., and Somerville, C. (1991) *Proc. Natl. Acad. Sci. U.S.A.* 88, 2510–2514.
14. Thompson, G. A., Scherer, D. E., Foxall-Van Aken, S., Kenny, J. W., Young, H. L., Shintani, D. K. Kridl, J. C., and Knauf, V. C. (1991) *Proc. Natl. Acad. Sci. U.S.A.* 88, 2578–2582.
15. Nishinda, I., Beppu, T., Matsuo, T., and Murata, N. (1992) *Plant Mol. Biol.* 19, 711–713.
16. Sato, A., Becker, C. K. and Kanuf, V. C. (1992) *Plant Physiol.* 99, 362–363.
17. Slocombe, S. P., Cummins, I., Jarvis, R. P., and Murphy, D. J. (1992) *Plant Mol. Biol.* 20, 151–155.
18. Taylor, M. A., Smith, S. B., Davies, H. V., and Burch, L. R. (1992) *Plant Physiol.* 100, 533–534.
19. Cahoon, E. B., Becker, C. K. Shanklin, J., and Ohlrogge, J. B. (1994) *Plant Physiol.,* in press.
20. Singh, S., McKinney, S., Green, A. (1994) Plant Physiol. 104, 1075.
21. Cahoon, E. B., Shanklin, J., and Ohlrogge, J. B. (1992) *Proc. Natl. Acad. Sci. U.S.A.* 89, 11184–11188.
22. Cahoon, E. B., and Ohlrogge, J. B. (1994) *Plant Physiol.* 104, 827–838.
23. Spencer, G. F., Kleiman, R., Miller, R. W., and Earle, F. R. (1971) *Lipids* 6, 712–714.
24. Morrison, W. R. and Smith, L. M. (1964) *J. Lipid Res.* 5, 600–608.
25. Cahoon, E. B., and Ohlrogge, J. B. (1994) *Plant Physiol.* 104, 845–855.
26. Christie, W. W. (1982) *Lipid Analysis,* 2nd Ed., Pergammon Press, Oxford.
27. Rock, C. O., and Garwin, J. L. (1979) *J. Biol. Chem.* 254, 7123–7128.
28. Hall, T. C., Ma. Y., Buchbinder, B. U., Pyne, J. W., Sun, S. M., and Bliss, F. A. (1978) *Proc. Natl. Acad. Sci. U.S.A.* 75, 3196–3200.
29. Hay, B., and Shod, J. M. (1992) *Strategies* 5, 16–18.
30. Sambrook, J., Fritsch, E. F., and Maniatis, T. (1989) *Molecular Clonging: a Laboratory Manual,* 2nd Ed., Cold Spring Harbor Laboratory, Cold Spring Harbor, N.Y.
31. Francis. G. W. (1981) *Chem. Phys. Lipids* 29, 369–374.
32. Yamamoto, K. Shibahara, A., Nakayama, T., and Kajimoto, G. (1991) *Chem. Phys. Lipdis* 60, 39–50.
33. Gibson, K. J. (1993) *Biochim. Biophys. Acta* 1169, 231–235.
34. Lütcke, H. A., Chow, K. C., Mickel, F. S., Moss, K. A., Kern, H. F., and Scheele, G. A. (1987) *EMBO J.* 6, 43–48.
35. Cronan Jr., J. E., and Rock, C. O. (1987) in *Escherichia coli and Salmonella typhimurium Cellular and Molecular Biology* (Neihardt, F. C., ed) pp. 474–497, American Society of Microbiology, Washington, D.C.
36. Studier, F. W., Rosenberg, A. H., Dunn, J. J., and Dubendorff, J. W. (1990) *Methods Enzymol.* 185, 60–89.
37. Schneider, G., Lindqvist, Y., Shanklin, J., and Somerville, C. (1992) *J. Mol. Biol.* 225, 561–564.
38. Rock, C. O., and Jackowski, S. (1982) *J. Biol. Chem.* 287, 10579–10765.
39. Knoell, H. E., and Knappe, J. (1974) *Eur. J. Biochem.* 50, 245–252.
40. Murphy, D. J. (1992) *Trends Biotechnol.* 10, 84–87.
41. Ohlrogge, J. B. (1992) *Plant Physiol.* 104, 821–826.
42. Schilperoort, R. A., Hoekema, A., and Hooykaas, P. J. J. (1990) U.S. Pat. No. 4,940,838.
43. Tomes, D., Bidney, D., Buising C. M. (1994) U. S. Pat. No. 5,322,783.
44. Bubeck, D. M., Fehr, W. R. and Hammond, E. G. (1980) *Crop. Sci.* 29, 652–656.
45. Perrson, C. (1985) *Cruciferae Newsletter* 10, p. 137, Scottish Crop Research Institute, Invergowerie, Dundee, Scotland.
46. Dörmann, P., Frentzen, M., and Ohlrogge, J. B. (1994) *Plant Physiol.* 104, 839–844.

What is claimed is:

1. An isolated plant $\Delta^6$-palmitoyl-acyl carrier protein desaturase.

2. An isolated protein having the amino acid sequence of SEQ ID NO 2.

3. An isolated *Thunbergia alata* $\Delta^6$-palmitoyl-acyl carrier protein desaturase.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 1258 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
ATTTTGTAAA GTGAAAATGG CATTGGTATT CAAGAGTATA GGAGCCCATA AGACTCCTCC      60

TTGTACTTTA AATTTAGCTT CACCAGCTTT GTACCACACC AGAGTCACAA TGGCTTCGAC     120

TATTACTCAC CCTCCGCCAC TCAAAGATAG AAAAATATCG TCTACTCGAC GAGTAAGGAC     180

ATATCCGTTG GCTCCAGAGA AGGCTGAAAT CTTCAATTCT ATGCACGGGT GGGTTGAAGA     240

CACCATTCTC CCTTTCCTGA AGCCGGTGGA GGAGTCGTGG CAGCCGACGG ACTTCCTCCC     300
```

```
GGACTCCACT TCTGATGGGT TCCACGAGCA AGTGGAAGAG CTTCGTAAAC GAACGGCCGA      360

TCTCCCTGAT GATTACTTAG TTGCATTGGT GGGAGCAATG GTGACGGAGG AAGCCCTTCC      420

GACGTATCAA ACAATGCTTA ACACGACAGA TGTGATATAC GATGAGAGCG GCGCCAGCCC      480

TGTGCCTTGG GCCGTTTGGA CCCGGGCTTG GACCGCTGAA GAGAACAGGC ATGGTGATAT      540

TGTCAACAAG TATCTCTATC TTTCCGGTCG TGTCGATATG AAGCAAATTG AGAAGACTAT      600

TCAATACTTG ATTGGCTCGG GCATGGATCC TGGTGCGGAC AACAACCCGT ACCTAGCATA      660

TATCTACACG TCGTATCAGG AGAGGGCTAC AGCGATCTCC CATGGAAGTC TGGGCCGGCT      720

AGCGAGGCAG AAGGGAGAGA TGAAACTGGC TCAGATTTGT GGAACAATTT CTGCCGATGA      780

GAAGCGGCAC GAGGCGGCGT ACTCGAAAAT CGTGGAGAAG CTATTCGAGT TGGATCCAGA      840

AGGCACAATG TTGGCGTTGG CATACATGAT GAAGATGAAG ATTGTAATGC CAGCTCGTCT      900

GATGCACGAT GGGAAGGATC CGGACATGTT TCAACATTTC CTGCTGTGT CGCAGCGACT      960

GGGGATTTAC ACTGCAAAGG AGTATACGGA CATTCTGGAG CATATGATAG CGCGGTGGGG     1020

AGTGGATAAG CTGACGGGGC TGAGCGGGGA GGGCCGCAGG GCGCAGGATT ACGTGTGCGG     1080

GTTGCCGATG AGGTTTAGGA AGGTGGAGGA GAGGGCGCAG GCGTGGGCGG AGAATATATC     1140

GCATGTTCCT TTTAGCTGGA TCTTTGGGAG AAGAGTGTAG TCTCAGTCTC AGTCTCACTC     1200

GGTCACTGTG TTGTTTGTTC TATGATCAAG AAATAAGTGC AATGCCACCC TTATTCTC      1258
```

( 2 ) INFORMATION FOR SEQ ID NO:2:

( i ) SEQUENCE CHARACTERISTICS:
        ( A ) LENGTH: 387 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

```
Met Ala Leu Val Phe Lys Ser Ile Gly Ala His Lys Thr Pro Pro Cys
 1               5                  10                  15

Thr Leu Asn Leu Ala Ser Pro Ala Leu Tyr His Thr Arg Val Thr Met
             20                  25                  30

Ala Ser Thr Ile Thr His Pro Pro Leu Lys Asp Arg Lys Ile Ser
         35                  40                  45

Ser Thr Arg Arg Val Arg Thr Tyr Pro Leu Ala Pro Glu Lys Ala Glu
     50                  55                  60

Ile Phe Asn Ser Met His Gly Trp Val Glu Asp Thr Ile Leu Pro Phe
 65                  70                  75                  80

Leu Lys Pro Val Glu Glu Ser Trp Gln Pro Thr Asp Phe Leu Pro Asp
                 85                  90                  95

Ser Thr Ser Asp Gly Phe His Glu Gln Val Glu Glu Leu Arg Lys Arg
            100                 105                 110

Thr Ala Asp Leu Pro Asp Asp Tyr Leu Val Ala Leu Val Gly Ala Met
        115                 120                 125

Val Thr Glu Glu Ala Leu Pro Thr Tyr Gln Thr Met Leu Asn Thr Thr
    130                 135                 140

Asp Val Ile Tyr Asp Glu Ser Gly Ala Ser Pro Val Pro Trp Ala Val
145                 150                 155                 160

Trp Thr Arg Ala Trp Thr Ala Glu Glu Asn Arg His Gly Asp Ile Val
                165                 170                 175

Asn Lys Tyr Leu Tyr Leu Ser Gly Arg Val Asp Met Lys Gln Ile Glu
            180                 185                 190
```

```
Lys Thr Ile Gln Tyr Leu Ile Gly Ser Gly Met Asp Pro Gly Ala Asp
            195                 200             205

Asn Asn Pro Tyr Leu Ala Tyr Ile Tyr Thr Ser Tyr Gln Glu Arg Ala
        210                 215             220

Thr Ala Ile Ser His Gly Ser Leu Gly Arg Leu Ala Arg Gln Lys Gly
225                 230                 235                 240

Glu Met Lys Leu Ala Gln Ile Cys Gly Thr Ile Ser Ala Asp Glu Lys
                245                 250             255

Arg His Glu Ala Ala Tyr Ser Lys Ile Val Glu Lys Leu Phe Glu Leu
            260                 265             270

Asp Pro Glu Gly Thr Met Leu Ala Leu Ala Tyr Met Met Lys Met Lys
            275                 280             285

Ile Val Met Pro Ala Arg Leu Met His Asp Gly Lys Asp Pro Asp Met
            290                 295             300

Phe Gln His Phe Ser Ala Val Ser Gln Arg Leu Gly Ile Tyr Thr Ala
305                 310                 315                 320

Lys Glu Tyr Thr Asp Ile Leu Glu His Met Ile Ala Arg Trp Gly Val
                325                 330             335

Asp Lys Leu Thr Gly Leu Ser Gly Glu Gly Arg Arg Ala Gln Asp Tyr
            340                 345             350

Val Cys Gly Leu Pro Met Arg Phe Arg Lys Val Glu Glu Arg Ala Gln
            355                 360             365

Ala Trp Ala Glu Asn Ile Ser His Val Pro Phe Ser Trp Ile Phe Gly
    370                 375             380

Arg Arg Val
385
```

( 2 ) INFORMATION FOR SEQ ID NO:3:

( i ) SEQUENCE CHARACTERISTICS:
        ( A ) LENGTH: 396 amino acids
        ( B ) TYPE: amino acid
        ( C ) STRANDEDNESS:
        ( D ) TOPOLOGY: linear ( x i ) SEQUENCE DESCRIPTION: SEQ ID NO:3:

```
Met Ala Leu Lys Leu Asn Pro Phe Leu Ser Gln Thr Gln Lys Leu Pro
1               5                   10                  15

Ser Phe Ala Leu Pro Pro Met Ala Ser Thr Arg Ser Pro Lys Phe Tyr
            20                  25                  30

Met Ala Ser Thr Leu Lys Ser Gly Ser Lys Glu Val Glu Asn Leu Lys
            35                  40                  45

Lys Pro Phe Met Pro Pro Arg Glu Val His Val Gln Val Thr His Ser
    50                  55                  60

Met Pro Pro Gln Lys Ile Glu Ile Phe Lys Ser Leu Asp Asn Trp Ala
65                  70                  75                  80

Glu Glu Asn Ile Leu Val His Leu Lys Pro Val Glu Lys Cys Trp Gln
                85                  90                  95

Pro Gln Asp Phe Leu Pro Asp Pro Ala Ser Asp Gly Phe Ala Glu Gln
            100                 105                 110

Val Arg Glu Leu Arg Glu Arg Ala Lys Glu Ile Pro Asp Asp Tyr Phe
            115                 120                 125

Val Val Leu Val Gly Asp Met Ile Thr Glu Glu Ala Leu Pro Thr Tyr
            130                 135                 140

Gln Thr Met Leu Asn Thr Leu Asp Gly Val Arg Asp Glu Thr Gly Ala
145                 150                 155                 160
```

Ser Pro Thr Ser Trp Ala Ile Trp Thr Arg Ala Trp Thr Ala Glu Glu
                165                 170                 175

Asn Arg His Gly Asp Leu Leu Asn Lys Tyr Leu Tyr Leu Ser Gly Arg
            180                 185                 190

Val Asp Met Arg Gln Ile Glu Lys Thr Ile Gln Tyr Leu Ile Gly Ser
        195                 200                 205

Gly Met Asp Pro Arg Thr Glu Asn Ser Pro Tyr Leu Gly Phe Ile Tyr
    210                 215                 220

Thr Ser Phe Gln Glu Arg Ala Thr Phe Ile Ser His Gly Asn Thr Ala
225                 230                 235                 240

Arg Gln Ala Lys Glu His Gly Asp Ile Lys Leu Ala Gln Ile Cys Gly
                245                 250                 255

Thr Ile Ala Ala Asp Glu Lys Arg His Glu Thr Ala Tyr Thr Lys Ile
            260                 265                 270

Val Glu Lys Leu Phe Glu Ile Asp Pro Asp Gly Thr Val Leu Ala Phe
        275                 280                 285

Ala Asp Met Met Arg Lys Lys Ile Ser Met Pro Ala His Leu Met Tyr
    290                 295                 300

Asp Gly Arg Asp Asp Asn Leu Phe Asp His Phe Ser Ala Val Ala Gln
305                 310                 315                 320

Arg Leu Gly Val Tyr Thr Ala Lys Asp Tyr Ala Asp Ile Leu Glu Phe
                325                 330                 335

Leu Val Gly Arg Trp Lys Val Asp Lys Leu Thr Gly Leu Ser Ala Glu
            340                 345                 350

Gly Gln Lys Ala Gln Asp Tyr Val Cys Arg Leu Pro Pro Arg Ile Arg
        355                 360                 365

Arg Leu Glu Glu Arg Ala Gln Gly Arg Ala Lys Glu Ala Pro Thr Met
    370                 375                 380

Pro Phe Ser Trp Ile Phe Asp Arg Gln Val Lys Leu
385                 390                 395

( 2 ) INFORMATION FOR SEQ ID NO:4:

( i ) SEQUENCE CHARACTERISTICS:
( A ) LENGTH: 385 amino acids
( B ) TYPE: amino acid
( C ) STRANDEDNESS:
( D ) TOPOLOGY: linear ( x i ) SEQUENCE DESCRIPTION: SEQ ID NO:4:

Met Ala Met Lys Leu Asn Ala Leu Met Thr Leu Gln Cys Pro Lys Arg
1               5                   10                  15

Asn Met Phe Thr Arg Ile Ala Pro Pro Gln Ala Gly Arg Val Arg Ser
            20                  25                  30

Lys Val Ser Met Ala Ser Thr Leu His Ala Ser Pro Leu Val Phe Asp
        35                  40                  45

Lys Leu Lys Ala Gly Arg Pro Glu Val Asp Glu Leu Phe Asn Ser Leu
    50                  55                  60

Glu Gly Trp Ala Arg Asp Asn Ile Leu Val His Leu Lys Ser Val Glu
65                  70                  75                  80

Asn Ser Trp Gln Pro Gln Asp Tyr Leu Pro Asp Pro Thr Ser Asp Ala
                85                  90                  95

Phe Glu Asp Gln Val Lys Glu Met Arg Glu Arg Ala Lys Asp Ile Pro
            100                 105                 110

Asp Glu Tyr Phe Val Val Leu Val Gly Asp Met Ile Thr Glu Glu Ala
        115                 120                 125

-continued

```
Leu Pro Thr Tyr Met Ser Met Leu Asn Arg Cys Asp Gly Ile Lys Asp
    130             135                 140
Asp Thr Gly Ala Gln Pro Thr Ser Trp Ala Thr Trp Thr Arg Ala Trp
145                 150                 155                 160
Thr Ala Glu Glu Asn Arg His Gly Asp Leu Leu Asn Lys Tyr Leu Tyr
            165                 170                 175
Leu Ser Gly Arg Val Asp Met Arg Met Ile Glu Lys Thr Ile Gln Tyr
            180                 185                 190
Leu Ile Gly Ser Gly Met Asp Thr Lys Thr Glu Asn Cys Pro Tyr Met
        195                 200                 205
Gly Phe Ile Tyr Thr Ser Phe Gln Glu Arg Ala Thr Phe Ile Ser His
    210                 215                 220
Ala Asn Thr Ala Lys Leu Ala Gln His Tyr Gly Asp Lys Asn Leu Ala
225                 230                 235                 240
Gln Val Cys Gly Asn Ile Ala Ser Asp Glu Lys Arg His Ala Thr Ala
            245                 250                 255
Tyr Thr Lys Ile Val Glu Lys Leu Ala Glu Ile Asp Pro Asp Thr Thr
            260                 265                 270
Val Ile Ala Phe Ser Asp Met Met Arg Lys Lys Ile Gln Met Pro Ala
        275                 280                 285
His Ala Met Tyr Asp Gly Ser Asp Asp Met Leu Phe Lys His Phe Thr
    290                 295                 300
Ala Val Ser Gln Gln Ile Gly Val Tyr Ser Ala Trp Asp Tyr Cys Asp
305                 310                 315                 320
Ile Leu Asp Phe Leu Val Asp Lys Trp Asn Val Ala Lys Met Thr Gly
            325                 330                 335
Leu Ser Gly Glu Gly Arg Lys Ala Gln Glu Tyr Val Cys Ser Leu Ala
            340                 345                 350
Ala Lys Ile Arg Arg Val Glu Glu Lys Val Gln Gly Lys Glu Lys Lys
        355                 360                 365
Ala Val Leu Pro Val Ala Phe Ser Trp Ile Phe Asn Arg Gln Ile Ile
370                 375                 380
Ile
385
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGNGA Y ATGA THACNGARGA          20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

ARRTATTGDA TNGT Y TT Y TC          20

( 2 ) INFORMATION FOR SEQ ID NO:7:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:7:

CAUCAUCAUC AU                   12

( 2 ) INFORMATION FOR SEQ ID NO:8:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:8:

CUACUACUAC UA                   12

( 2 ) INFORMATION FOR SEQ ID NO:9:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:9:

GCTTCGACTA TTACTCAC                18

( 2 ) INFORMATION FOR SEQ ID NO:10:

( i ) SEQUENCE CHARACTERISTICS:
  ( A ) LENGTH: 7 amino acids
  ( B ) TYPE: amino acid
  ( C ) STRANDEDNESS:
  ( D ) TOPOLOGY: linear ( x i ) SEQUENCE DESCRIPTION: SEQ ID NO:10:

Gly Asp Met Ile Thr Glu Glu
 1     5

( 2 ) INFORMATION FOR SEQ ID NO:11:

( i ) SEQUENCE CHARACTERISTICS:
  ( A ) LENGTH: 7 amino acids
  ( B ) TYPE: amino acid
  ( C ) STRANDEDNESS:
  ( D ) TOPOLOGY: linear ( x i ) SEQUENCE DESCRIPTION: SEQ ID NO:11:

Ile Glu Gln Thr Ile Tyr Leu
 1     5

( 2 ) INFORMATION FOR SEQ ID NO:12:

( i ) SEQUENCE CHARACTERISTICS:
  ( A ) LENGTH: 7 amino acids
  ( B ) TYPE: amino acid
  ( C ) STRANDEDNESS:
  ( D ) TOPOLOGY: linear ( x i ) SEQUENCE DESCRIPTION: SEQ ID NO:12:

Glu Lys Thr Ile Gln Tyr Leu
 1     5